(12) United States Patent
Ogasawara

(10) Patent No.: US 8,878,921 B2
(45) Date of Patent: Nov. 4, 2014

(54) IMAGING SYSTEM

(71) Applicant: Olympus Medical Systems Corp., Tokyo (JP)

(72) Inventor: Kotaro Ogasawara, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/062,113

(22) Filed: Oct. 24, 2013

(65) Prior Publication Data

US 2014/0104403 A1 Apr. 17, 2014

Related U.S. Application Data

(63) Continuation of application No. PCT/JP2013/062112, filed on Apr. 24, 2013.

(30) Foreign Application Priority Data

Apr. 26, 2012 (JP) .................................. 2012-100893

(51) Int. Cl.
*A61B 1/04* (2006.01)
*A61B 1/06* (2006.01)

(52) U.S. Cl.
CPC ............ *H04N 7/183* (2013.01); *A61B 1/00009* (2013.01); *H04N 5/2354* (2013.01); *A61B 1/04* (2013.01); *A61B 1/00096* (2013.01); *A61B 1/005* (2013.01); *G02B 23/2484* (2013.01); *A61B 1/00117* (2013.01); *H04N 2005/2255* (2013.01); *A61B 1/00045* (2013.01); *A61B 1/00114* (2013.01); *A61B 1/0669* (2013.01); *A61B 1/051* (2013.01); *G02B 23/2461* (2013.01); *A61B 1/00006* (2013.01); *A61B 1/07* (2013.01)
USPC ........... 348/68; 348/294; 348/302; 205/208.1

(58) Field of Classification Search
CPC ................ H04N 7/183; H04N 5/2354; H04N 2005/2255; A61B 1/0669; A61B 1/051; A61B 1/00006; A61B 1/005; A61B 1/00009; A61B 1/00045; A61B 1/00114; A61B 1/00117; A61B 1/07; A61B 1/00096; A61B 1/04; G02B 23/2484; G02B 23/2461
See application file for complete search history.

(56) References Cited

U.S. PATENT DOCUMENTS 7,223,956 B2    5/2007  Yoshida
2005/0178950 A1* 8/2005  Yoshida ..................... 250/208.1

FOREIGN PATENT DOCUMENTS

JP    2005-236513 A    9/2005
JP    2007-318581 A    12/2007

(Continued)

OTHER PUBLICATIONS

International Search Report dated Aug. 6, 2013 from related International Application No. PCT/JP2013/062112, together with an English language translation.

(Continued)

*Primary Examiner* — Joseph Ustaris
*Assistant Examiner* — Jill Sechser
(74) *Attorney, Agent, or Firm* — Scully, Scott, Murphy & Presser, PC

(57) ABSTRACT

An imaging system includes: an illumination unit that emits illumination light to illuminate a subject; a light receiving unit in which pixels that receive light and photoelectrically convert the received light to generate an electric signal are two-dimensionally arranged; a read unit that sequentially reads the electric signal from the pixels for each horizontal line; and an illumination controller that controls the illumination unit to emit a pulse of the illumination light during a period straddling a read period of the read unit for a first horizontal line and a read period for a second horizontal line which is adjacent to the first horizontal line and which is read immediately after the first horizontal line.

3 Claims, 3 Drawing Sheets

(51) Int. Cl.
*A61B 1/05* (2006.01)
*H04N 3/14* (2006.01)
*H01L 27/00* (2006.01)
*H04N 7/18* (2006.01)
*H04N 5/235* (2006.01)
*A61B 1/00* (2006.01)
*A61B 1/005* (2006.01)
*A61B 1/07* (2006.01)
*G02B 23/24* (2006.01)
*H04N 5/225* (2006.01)

(56) References Cited

FOREIGN PATENT DOCUMENTS

| | | |
|---|---|---|
| JP | 2010-278728 A | 12/2010 |
| JP | 2011-250926 A | 12/2011 |
| WO | 2010/119669 A1 | 10/2010 |

OTHER PUBLICATIONS

Decision of a Patent Grant dated Jan. 7, 2014 from related Japanese Application No. 2013-546471, together with an English language translation.

\* cited by examiner

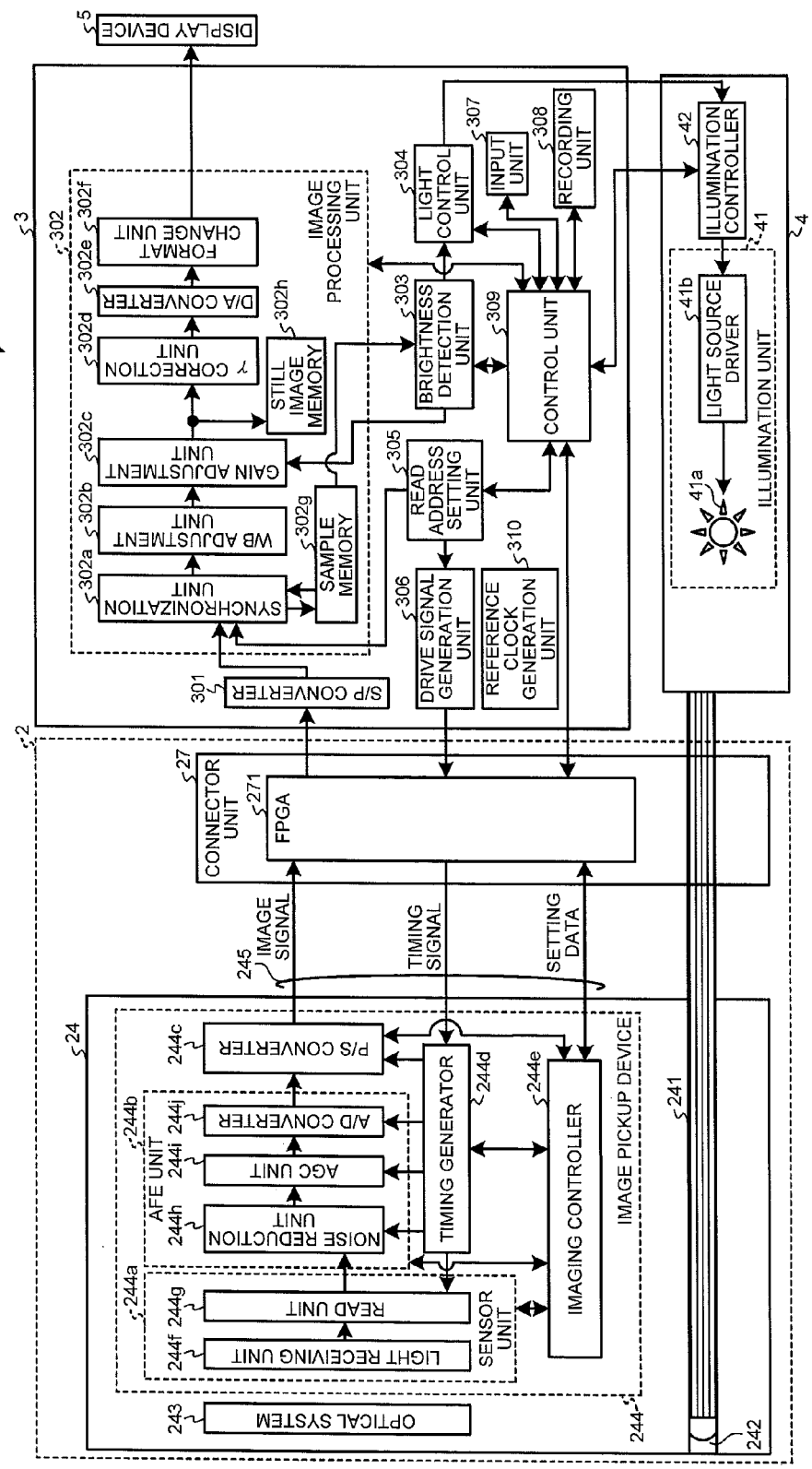

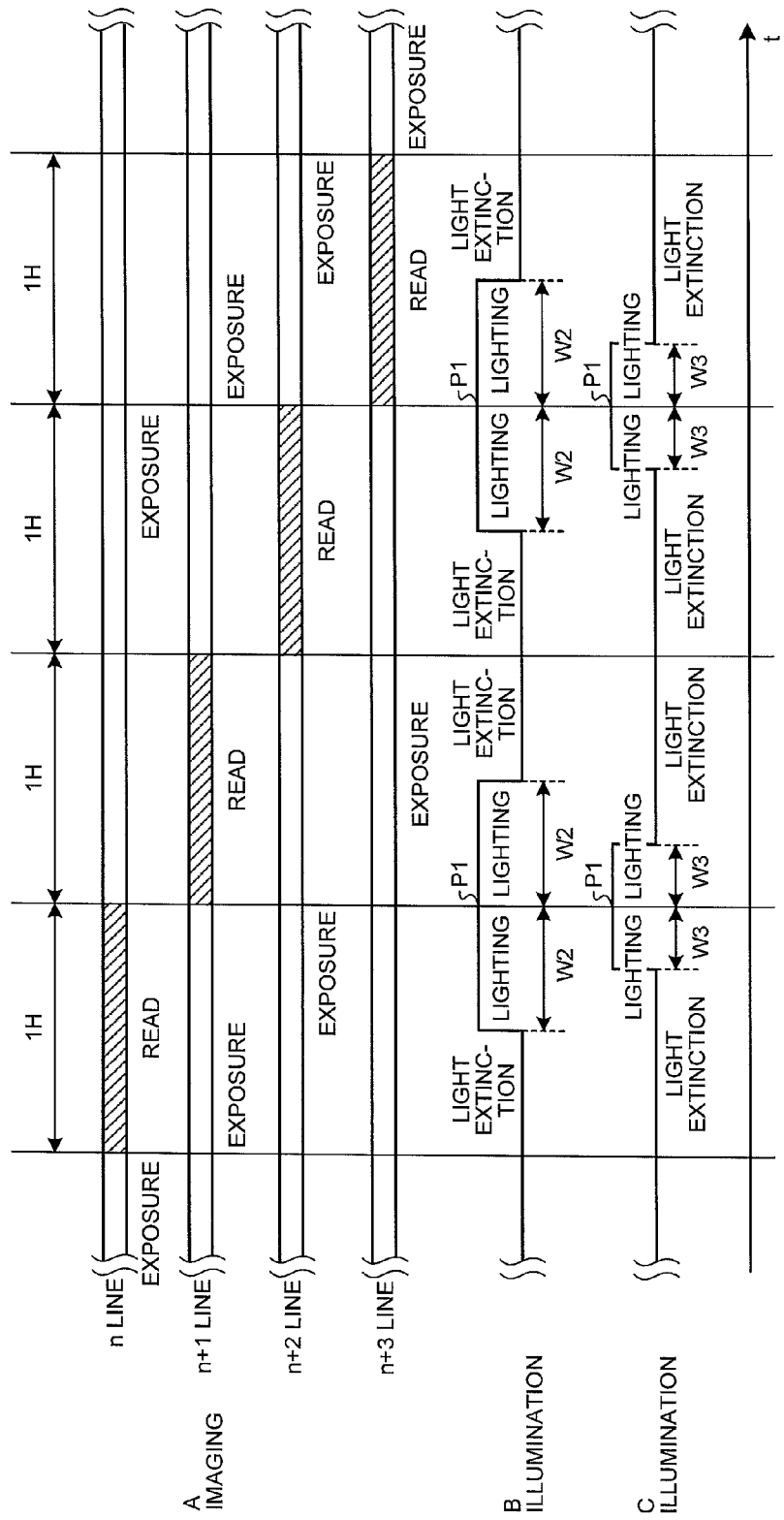

IMAGING SYSTEM

CROSS REFERENCES TO RELATED APPLICATIONS

This application is a continuation of PCT international application Ser. No. PCT/JP2013/062112 filed on Apr. 24, 2013 which designates the United States, incorporated herein by reference, and which claims the benefit of priority from Japanese Patent Application No. 2012-100893, filed on Apr. 26, 2012, incorporated herein by reference.

BACKGROUND OF THE INVENTION

1. Field of the Invention

The present invention relates to an imaging system capable of outputting, as image information, a photoelectrically converted electric signal from a pixel arbitrarily specified as a read target from among a plurality of pixels for imaging.

2. Description of the Related Art

In a medical field, an endoscope system has conventionally been used for observing an organ of a subject such as a patient. The endoscope system includes an imaging device (electronic scope) that has flexibility and an elongated shape and is configured to be inserted into a body cavity of the subject, an image pickup device that is provided at a distal end of the imaging device and captures an in-vivo image, a light source device that emits illumination light to illuminate the subject, a processing device (external processor) that performs specified image processing on the in-vivo image captured by the image pickup device, and a display device capable of displaying the in-vivo image that has been subjected to the image processing by the processing device. In acquiring the in-vivo image using the endoscope system, after an insertion unit is inserted into the body cavity of the subject, the illumination light is emitted from a distal end of the insertion unit to illuminate body tissue in the body cavity, and the image pickup device captures the in-vivo image. A user such a doctor observes an organ of the subject based on the in-vivo image displayed on the display device.

A CMOS (Complementary Metal Oxide Semiconductor) sensor can be used as the image pickup device to be provided in such an endoscope system. A CMOS sensor generates image data according to a rolling shutter method in which exposure or readout is carried out for each line at different timings.

Further, in order to prevent degradation in image quality due to exposure unevenness between the lines of the image pickup device, there is known a technique in which lighting and light extinction of illumination are performed in a specified cycle under a PWM (Pulse Width Modulation) control in synchronization with the exposure cycle or readout cycle of the image pickup device (see Japanese Laid-open Patent Publication No. 2007-318581).

SUMMARY OF THE INVENTION

An imaging system according to one aspect of the invention includes: an illumination unit that emits illumination light to illuminate a subject; a light receiving unit in which pixels that receive light and photoelectrically convert the received light to generate an electric signal are two-dimensionally arranged; a read unit that sequentially reads the electric signal from the pixels for each horizontal line; and an illumination controller that controls the illumination unit to emit a pulse of the illumination light during a period straddling a read period of the read unit for a first horizontal line and a read period for a second horizontal line which is adjacent to the first horizontal line and which is read immediately after the first horizontal line.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a block diagram illustrating a functional configuration of a main part of the endoscope system according to the embodiments of the present invention; and FIG. 3 is a schematic view illustrating a relationship between exposure timing or read timing of an image pickup device and lighting timing or light extinction timing of a light source device at time of imaging by the endoscope system according to the embodiments of the present invention.

DETAILED DESCRIPTION OF THE PREFERRED EMBODIMENTS

Figure 1:
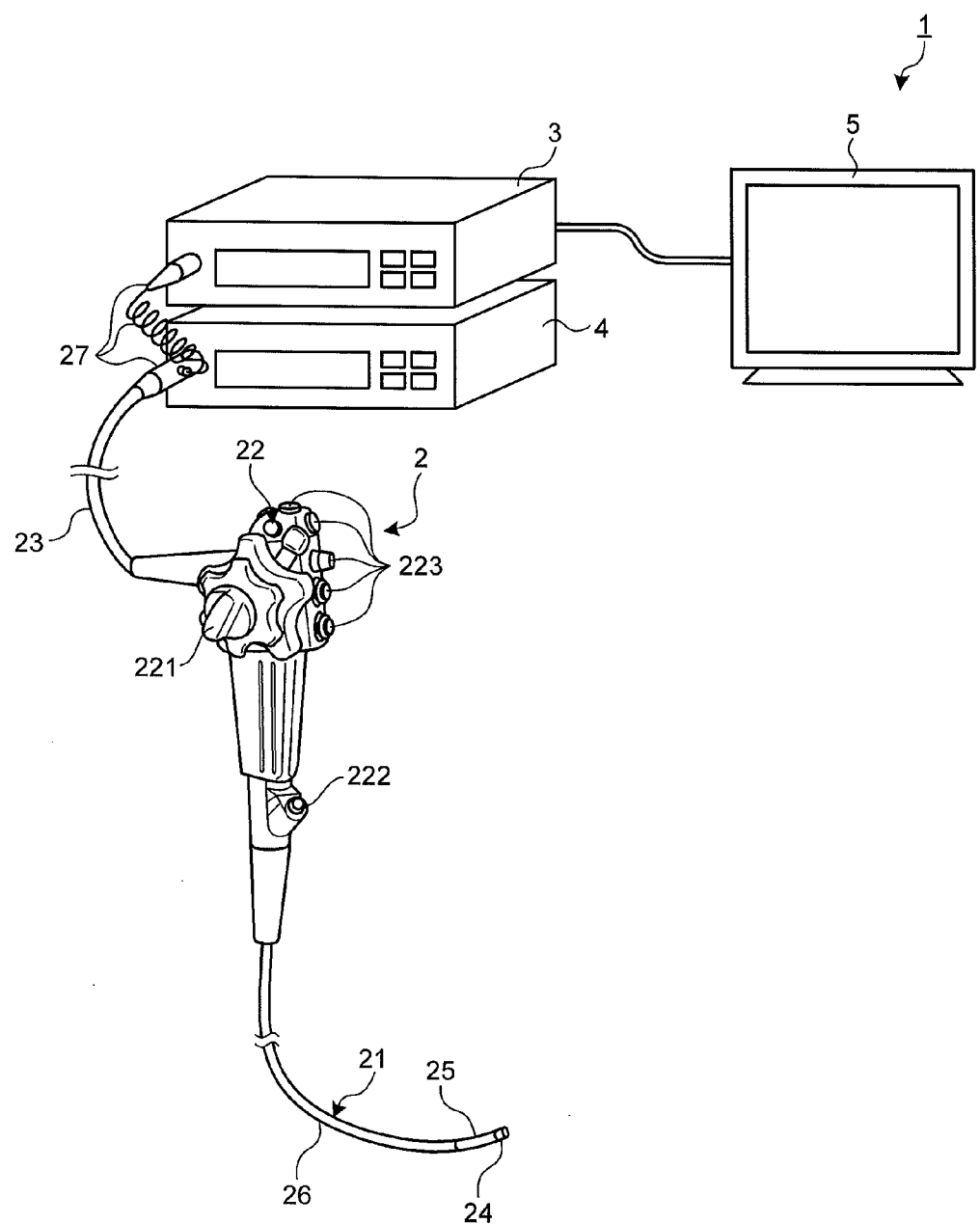
FIG. 1 is a schematic view illustrating a configuration of an endoscope system according to embodiments of the present invention.

As modes for carrying out the invention (hereinafter referred to as "embodiments"), a medical endoscope system that captures and displays an image inside a body cavity of a subject, such as a patient, will be described below as an imaging system. It should be noted that the following description does not limit the invention. Throughout the accompanying drawings, the same reference numerals are used to designate the identical or similar components.

FIG. 1 is a schematic view illustrating a configuration of an endoscope system according to embodiments of the present invention. FIG. 2 is a block diagram illustrating a functional configuration of a main part of the endoscope system according to the embodiments of the present invention.

As illustrated in FIGS. 1 and 2, an endoscope system 1 includes an endoscope 2 (electronic scope) whose distal end is configured to be inserted into a body cavity of a subject to capture an in-vivo image of the subject, a processing device 3 (external processor) that performs specified image processing on the in-vivo image captured by the endoscope 2 and controls the overall operation of the endoscope system 1, a light source device 4 that generates illumination light to be emitted from the distal end of the endoscope 2, and a display device 5 that displays the in-vivo image that has been subjected to the image processing by the processing device 3.

The endoscope 2 includes an insertion unit 21 having flexibility and an elongated shape, an operation unit 22 that is connected to a proximal end side of the insertion unit 21 and receives an input of various operation signals, and an universal cord 23 that extends from the operation unit 22 in a direction different from an extending direction of the insertion unit 21 and incorporates various cables to be connected to the processing device 3 and light source device 4.

The insertion unit 21 includes a distal end portion 24 that incorporates an image pickup device 244 in which pixels that receive and photoelectrically convert light to generate a signal are two-dimensionally arranged, a freely bendable bent portion 25 constituted by a plurality of bending pieces, and an elongated flexible tube portion 26 connected to a proximal end side of the bent portion 25.

The distal end portion 24 includes a light guide 241 that is formed by using a glass fiber or the like and serving as a light guide path for guiding light emitted from the light source device 4, an optical system 243 for light collection, and the image pickup device 244 that is provided at an imaging position of the optical system 243 and that receives light collected by the optical system 243, photoelectrically converts the received light into an electric signal, and applies specified signal processing to the obtained electric signal.

The optical system 243 is constituted by one or more lenses and has an optical zooming function that changes a filed angle and a focusing function that changes a focal point.

The image pickup device 244 includes a sensor unit 244a that photoelectrically converts the light from the optical system 243 and outputs an electric signal, an analog front-end unit 244b (hereinafter, referred to as "AFE unit 244b") that applies noise reduction and A/D conversion to the electric signal output from the sensor unit 244a, a P/S converter 244c that performs a parallel/serial conversion of a digital signal (image signal) output from the AFE unit 244b and transmits the resultant signal to the outside, a timing generator 244d that generates timing for driving the sensor unit 244a and pulses for various signal processing to be performed in the AFE unit 244b and P/S converter 244c, and an imaging controller 244e that controls operation of the image pickup device 244. The image pickup device 244 is a CMOS sensor.

The sensor unit 244a includes a light receiving unit 244f and a read unit 244g. In the light receiving unit 244f, a plurality of pixels each having a photodiode for storing an electric charge depending on a light amount and an amplifier for amplifying the charge stored in the photodiode are two-dimensionally arranged. The read unit 244g sequentially reads, for each horizontal line, an electric signal as image information from a pixel arbitrarily specified as a read target from among the plurality of pixels in the light receiving unit 244f. A light receiving surface of the light receiving unit 244f is provided with a color filter corresponding to each pixel.

The AEF unit 244b includes a noise reduction unit 244h that reduces a noise component included in an electric signal (analog signal), an AGC (Auto Gain Control) unit 244i that controls an amplification rate (gain) of the electric signal so as to maintain a constant output level, and an A/D converter 244j that A/D converts the electric signal as image information (image signal) output through the AGC unit 244i. The noise reduction unit 244h reduces noise by using, e.g., a correlated double sampling method.

The imaging controller 244e controls various operations of the distal end portion 24 according to setting data received from the processing device 3. The imaging controller 244e includes a CPU (Central Processing device), a register that records therein various programs, and the like.

The operation unit 22 includes: a bending knob 221 for bending the bent portion 25 in vertical and horizontal directions; a treatment tool insertion portion 222 through which a treatment tool such as a pair of biopsy forceps, a laser scalpel, or an inspection probe is inserted into a body cavity of a subject; and a plurality of switches 223 serving as an operation input unit that inputs thereto an operation instruction signal with respect to peripheral devices such as an air supply means, a water supply means, and a gas supply means, as well as the processing device 3 and light source device 4. The treatment tool inserted through the treatment tool insertion portion 222 is passed through a treatment tool channel (not illustrated) of the distal end portion 24 and is drawn out of an opening portion (not illustrated).

The universal cord 23 incorporates at least the light guide 241 and a cable assembly 245 including one or more signal lines. The universal cord 23 includes a connector unit 27 detachably attached to the processing device 3 and light source device 4.

The connector unit 27 includes an FPGA (Field Programmable Gate Array) 271. The FPGA 271 receives an electric signal from the image pickup device 244 and outputs the received electric signal to the processing device 3. The FPGA 271 may control individual components of the image pickup device 244 according to the setting data from the processing device 3.

Next, reference will now be made to a configuration of the processing device 3. The processing device 3 includes an S/P converter 301, an image processing unit 302, a brightness detection unit 303, a light control unit 304, a read address setting unit 305, a drive signal generation unit 306, an input unit 307, a recording unit 308, a control unit 309, and a reference clock generation unit 310.

The S/P converter 301 performs a serial/parallel conversion of an image signal (electric signal) input from the connector unit 27 and outputs the resultant signal to the image processing unit 302.

The image processing unit 302 generates, based on the image signal input from the S/P converter 301, an in-vivo image to be displayed by the display device 5. The image processing unit 302 includes a synchronization unit 302a, a white balance adjustment unit 302b (hereinafter, referred to as "WB adjustment unit 302b"), a gain adjustment unit 302c, a γ correction unit 302d, a D/A converter 302e, a format change unit 302f, a sample memory 302g, and a still image memory 302h.

The synchronization unit 302a synchronizes the image information input as pixel information. The synchronization unit 302a sequentially outputs synchronized RGB image information to the WB adjustment unit 302b and outputs a part of the RGB image information to the sample memory 302g as information for image analysis such as brightness detection.

The WB adjustment unit 302b automatically adjusts white balance of the RGB image information. Specifically, the WB adjustment unit 302b automatically adjusts the white balance of the RGB image information based on a color temperature included in the RGB image information.

The gain adjustment unit 302c performs a gain adjustment for the RGB image information. The gain adjustment unit 302c outputs the gain-adjusted RGB signal to the γ correction unit 302d and outputs a part of the RGB signal to the still image memory 302h as a signal for still image display, a signal for enlarged image display, or a signal for highlighted image display.

The γ correction unit 302d performs gray level correction (γ correction) for the RGB image information in correspondence with the display device 5.

The D/A converter 302e converts the gray scale corrected RGB image information output from the γ correction unit 302d into an analog signal.

The format change unit 302f changes the analog image information into a moving image file format, such as a Hi-Vision system, and outputs the resultant image information to the display device 5.

The brightness detection unit 303 detects a brightness level corresponding to each pixel from the RGB image information retained in the sample memory 302g, records the detected brightness level in a memory provided inside thereof, and outputs the same to the control unit 309. Further, the brightness detection unit 303 calculates a gain adjustment value and a light irradiation amount based on the detected brightness, and outputs the gain adjustment value and light irradiation amount to the gain adjustment unit 302c and light control unit 304, respectively.

The light control unit 304 sets an amount and emission timing of light to be generated by the light source device 4 under control of the control unit 309 based on the light irradiation amount calculated by the brightness detection unit 303, and outputs a light control signal including the set conditions to the light source device 4.

The read address setting unit 305 has a function of setting read target pixels on a light receiving surface of the sensor unit 244a and an order in which the read target pixels are read. That is, the read address setting unit 305 has a function of setting addresses of the pixels that the AFE unit 244b reads from the sensor unit 244a. Further, the read address setting unit 305 outputs address information of the set read target pixels to the synchronization unit 302a.

The drive signal generation unit 306 generates a drive timing signal for driving the image pickup device 244 under control of the control unit 309 and transmits the generated timing signal to the timing generator 244d through a specified signal line included in the cable assembly 245. The timing signal includes the address information of the read target pixels.

The input unit 307 receives an input of various signals such as operation instruction signals for instructing operation of the endoscope system 1.

The recording unit 308 is realized by using a semiconductor memory such as a flash memory or a DRAM (Dynamic Random Access Memory). The recording unit 308 records therein various programs required for operating the endoscope system 1 and data including parameters and the like required for operating the endoscope system 1. Further, the recording unit 308 records therein identification information of the processing device 3. The identification information herein includes unique information (ID), model year information, spec information, a transmission system, a transmission rate, and the like.

The control unit 309 is constituted by a CPU and the like, and performs drive control of individual components including the image pickup device 244 and light source device 4 and input/output control of information for the individual components. The control unit 309 transmits setting data for imaging control to the imaging controller 244e through a specified signal line included in the cable assembly 245. The control unit 309 outputs a synchronization signal including exposure timing and read timing of each line of the image pickup device 244 to the light source device 4.

The reference clock generation unit 310 generates a reference clock signal serving as a reference for the operation of the individual components of the endoscope system 1, and supplies the generated reference clock signal to the individual components of the endoscope system 1.

Next, reference will be made to a configuration of the light source device 4. The light source device 4 includes an illumination unit 41 and an illumination controller 42.

The illumination unit 41 emits illumination light to illuminate a subject. The illumination unit 41 includes a light source 41a and a light source driver 41b.

The light source 41a is constituted by a white LED and generates white light under control of the illumination controller 42. The light generated by the light source 41a is emitted from the distal end portion 24 toward the subject through a condenser lens (not illustrated) and light guide 241.

The light source driver 41b supplies current to the light source 41a under the control of the illumination controller 42 to cause the light source 41a to generate the white light.

The illumination controller 42 causes the illumination unit 41 to emit illumination light during a period which straddles the adjacent two lines in the light receiving unit 244f and which is a part of read periods of the read unit 244g with respect to adjacent lines in the light receiving unit 244f. The illumination controller 42 also controls illumination periods in the respective lines to be equal to each other at every two lines in the light receiving unit 244f to thereby cause the illumination periods for the respective lines in the light receiving unit 244f in one frame to be equal to each other. Specifically, the illumination controller 42 receives the synchronization signal and light control signal sent from the control unit 309 and the light control unit 304, respectively. Then, based on the received synchronization signal and light control signal, the illumination controller 42 controls electric energy that the light source driver 41b supplies to the light source 41a, and uses PWM control to control the drive timing at which the light source driver 41b drives the light source 41a.

The display device 5 receives, from the processing device 3, the in-vivo image generated by the processing device 3 through a video cable and displays the received in-vivo image. The display device 5 is constituted by liquid crystal or organic EL (Electro Luminescence).

Reference will now be made to a relationship between exposure timing or read timing of the image pickup device 244 and lighting timing or light extinction timing of the light source device 4 at time of imaging by the endoscope system 1 having the configuration described above.

FIG. 3 is a schematic view of a relationship between the exposure timing or the read timing of the image pickup device 244 and the lighting timing or the light extinction timing of the light source device 4 at the time of imaging by the endoscope system 1. In FIG. 3, a horizontal axis represents time. Symbol A of FIG. 3 represents the exposure timing or the read timing of each line in the image pickup device 244, and 1H represents a read period of each line. Symbol B of FIG. 3 represents the light extinction timing or the lighting timing of the light source device 4. Symbol C of FIG. 3 represents another example of the light extinction timing or the lighting timing of the light source device 4.

As illustrated in FIG. 3, the illumination controller 42 performs PWM control with respect to a lighting period of the illumination of the light source device 4 with a period of two lines in which the read unit 244g reads the image signal from the light receiving unit 244f. For example, the illumination controller 42 combines the two lines in which the read unit 244g reads the image signal from the light receiving unit 244f, into one set (one unit) and changes the lighting period of the illumination of the light source device 4 such that lighting time before a boundary between the two lines of the read timing and lighting time after the boundary are equal to each other to thereby cause the illumination periods for respective lines to be equal to each other.

As illustrated in B of FIG. 3, the illumination controller 42 causes the illumination unit 41 to emit illumination light during a period which straddles adjacent n line (n=natural number) and n+1 line in the light receiving unit 244f and which is a part of the read periods in the read unit 244g with respect to the adjacent n line and n+1 line. The illumination controller 42 causes illumination periods W2 for n line and n+1 line to be equal to each other at every two lines in the light receiving unit 244f to thereby cause the illumination periods for respective lines of the light receiving unit 244 in one frame to be equal to each other. Specifically, the illumination controller 42 sets a boundary between an end point of the read period of the read unit 244g for n line of the light receiving unit 244f and a start point of the read period for n+1 line as a reference P1, and causes the illumination period W2 for the n line from a specified time point to the reference P1 and the illumination period W2 for the n+1 line from the reference P1 to a specified time point to be equal to each other. That is, the light source 41a emits light (continuous lighting) such that the illumination periods W2 for n line and n+1 line are continued and, whereby, the number of times of switching between the lighting and light extinction for two lines can be reduced to one.

As illustrated in C of FIG. 3, the illumination controller 42 controls the illumination unit 41 to emit illumination light during a period which straddles the adjacent n line and n+1 line in the light receiving unit 244f and which is a part of the read periods of the read unit 244g with respect to the adjacent n line and n+1 line. The illumination controller 42 causes illumination periods W3 (W3<W2) for n line and n+1 line to be equal to each other at every two lines of the light receiving unit 244f to thereby cause the illumination periods for respective lines of the light receiving unit 244f in one frame to be equal to each other.

As described above, in the endoscope system 1, even when there is a limit to a switching speed of switching between the lighting and light extinction of the light source 41a, it is possible to reduce an exposure time for one line (see C of FIG. 3) by controlling the illumination period at every two lines, allowing expansion of a variable range of the exposure time (i.e., illumination control range).

According to the above-described embodiments of the present invention, the illumination controller 42 controls the illumination unit 41 to emit illumination light during a period which straddles the adjacent two lines in the light receiving unit 244f and which is a part of the read periods of the read unit 244g with respect to the adjacent lines. The illumination controller 42 also causes illumination periods for the respective lines to be equal to each other at every two lines of the light receiving unit 244f to thereby cause the illumination periods for the respective lines of the light receiving unit 244f in one frame to be equal to each other. As a result, even when there is a limit to a switching speed of switching between the lighting and light extinction of the illumination unit 41, it is possible to prevent exposure unevenness and to expand the illumination control range.

Further, according to the embodiments of the present invention, the exposure time of the image pickup device 244 by an electronic shutter and emission amount of the illumination light from the light source device 4 can be controlled independently of each other, thus finer brightness control can be achieved.

Further, the present invention can be applied also to a light source device of a field sequential system that sequentially emits light having different wavelengths.

Further, the present invention can be applied also to a case where the light source device 4 emits NBI (Narrow Band Imaging) illumination light of two bands, which are different in wavelength band from the white illumination light, e.g., blue light (e.g., 400 nm to 500 nm) and green light (e.g., 500 nm to 600 nm) whose band is narrowed by a narrow-band bandpass filter.

Further, in the present invention, the processing device 3 and light source device 4 may be integrally provided.

Further, in the present invention, an LED may be provided at the distal end portion 24 as the illumination unit, and the imaging controller 244e or the FPGA 271 may control the LED.

Further, in the present invention, the control unit 309 may perform the PWM control for the lighting/extinction of the illumination unit 41 based on the light control signal and the exposure or read timing of the image pickup device 244.

Further, the present invention can be applied also to a case where a read period of the read unit 244g from the light receiving unit 244f is a one-field period.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
an illumination unit that emits illumination light to illuminate a subject;
a light receiving unit in which pixels that receive light and photoelectrically convert the received light to generate an electric signal are two-dimensionally arranged;
a read unit that sequentially reads the electric signal from the pixels for each horizontal line; and
an illumination controller that controls the illumination unit to emit a pulse of the illumination light whose center is positioned at an end point of a read period for a first horizontal line, during a period straddling the read period of the read unit for the first horizontal line and a read period for a second horizontal line which is adjacent to the first horizontal line and which is read immediately after the first horizontal line.

2. The imaging system according to claim 1, wherein control by the illumination controller is carried out at every two horizontal lines.

3. The imaging system according to claim 1, further comprising a brightness detection unit that detects brightness of light received by the light receiving unit, wherein
based on a detection result by the brightness detection unit, the illumination controller performs PWM control for varying a pulse width of the pulse of the illumination light whose center is positioned at the end point of the read period for the first horizontal line.

* * * * *